(12) United States Patent
Bjork, Jr.

(10) Patent No.: US 8,168,184 B2
(45) Date of Patent: May 1, 2012

(54) BI-SPECIFIC MONOCLONAL ANTIBODY (SPECIFIC FOR BOTH CD3 AND CD11B) THERAPEUTIC DRUG

(76) Inventor: Robert Lamar Bjork, Jr., San Diego, CA (US)

(*) Notice: Subject to any disclaimer, the term of this patent is extended or adjusted under 35 U.S.C. 154(b) by 49 days.

(21) Appl. No.: 12/510,923

(22) Filed: Jul. 28, 2009

(65) Prior Publication Data

US 2010/0008852 A1 Jan. 14, 2010

Related U.S. Application Data

(62) Division of application No. 11/821,127, filed on Jun. 22, 2007.

(60) Provisional application No. 60/834,816, filed on Jul. 29, 2006.

(51) Int. Cl.
*A61K 39/395* (2006.01)
*A61K 51/10* (2006.01)
*A61P 31/12* (2006.01)
*A61P 35/00* (2006.01)

(52) U.S. Cl. ............... 424/133.1; 424/1.49; 424/136.1; 424/174.1; 424/178.1

(58) Field of Classification Search .................. None
See application file for complete search history.

(56) References Cited

U.S. PATENT DOCUMENTS

| | | | |
|---|---|---|---|
| 5,234,816 | A | 8/1993 | Terstappen |
| 5,578,704 | A | 11/1996 | Kim et al. |
| 5,652,109 | A | 7/1997 | Kim et al. |
| 5,652,110 | A | 7/1997 | Kim et al. |
| 5,654,157 | A | 8/1997 | Kim |
| 5,658,570 | A | 8/1997 | Newman et al. |
| 5,688,003 | A | 11/1997 | Beale |
| 5,688,681 | A | 11/1997 | Kim |
| 5,980,894 | A | 11/1999 | Kim |
| 6,294,167 | B1 | 9/2001 | Lindhofer et al. |
| 6,359,126 | B1 | 3/2002 | Kim et al. |
| 6,369,204 | B1 | 4/2002 | Kim et al. |
| 6,448,075 | B1 | 9/2002 | Thomas et al. |
| 6,544,749 | B1 | 4/2003 | Kim |
| 2003/0134416 | A1 | 7/2003 | Yamanishi et al. |
| 2004/0005298 | A1* | 1/2004 | Bonyhadi et al. ........... 424/93.7 |
| 2004/0023377 | A1 | 2/2004 | Assenmacher et al. |
| 2005/0123536 | A1 | 6/2005 | Law et al. |
| 2006/0045881 | A1 | 3/2006 | Molldrem |
| 2006/0234226 | A1 | 10/2006 | Fahner et al. |
| 2007/0237779 | A1 | 10/2007 | Ledbetter et al. |

FOREIGN PATENT DOCUMENTS

DE 195 31 346 A1 2/1997

OTHER PUBLICATIONS

Bjork Jr. et al., "The clinical significance of CD8+ T cell subset abnormalities in common human malignancies", *Clinical and Applied Immunology Reviews* 2:141 (2002).

Chatila et al., "Constitutive and Stimulus-induced Phosphorylation of CD11/CD18 Leukocyte Adhesion Molecules", *The Journal of Cell Biology*, 109(No. 6, Pt. 2):3435-3444 (1989).
Clement et al, "Morphologic and Phenotypic Features of the Subpopulation of Leu-2 Cells That Suppresses B Cell Differentiation," *J. of Immunology*, 133(5):2461-2467 (1984).
Damle et. al., "Soluble Antigen-Primed Inducer T Cells Activate Antigen-Specific Suppressor T Cells in the Absence of Antigen-Pulsed Accessory Cells: Phenotypic Definition of Suppressor-Inducer and Suppressor-Effector Cells", *J. Immunology* 132(2):644 (1984).
Diamond & Springer, "A Subpopulation of Mac-1 (CD11b/CD18) Molecules Mediates Neutrophil Adhesion to ICAM-1 and Fibrinogen", *The Journal of Cell Biology*, 120(2):545-556 (1993).
Kundu & Merigan, "Inverse relationship of CD8+CD11+ suppressor T cells with human immunodeficiency virus (HIV)-specific cellular cytotoxicity and natural killer cell activity in HIV infection", *Immunology* 74:567 (1991).
Landay et al., "Characterization of a Phenotypically distinct subpopulation of leu-2+ cells that suppresses T Cell proliferative responses", *J. Immunology* 131(6):2757 (1983).
Lee et al., "Two conformations of the integrin A-domain (I-domain): a pathway for activation?", *Structure*, 3:1333-1340 (1995).
Platsoucas et al., "Abnormal T Lymphocyte subpopulations in patients with B cell chronic lymphocytic leukemia: an analysis by monoclonal antibodies", *J. Immunology* 129(5):2305 (1982).
The Encyclopedia of Molecular Biology, *Blackwell Science Ltd.*, p. 1052 (1994).
Dechant and Valerius, "IgA antibodies for cancer therapy", *Crit. Rev. Oncol. Hematol.*, 39(1-2):69-77 (2001).
Kontermann R.E., "Recombinant bispecific antibodies for cancer therapy", *Acta. Pharmacol. Sin.*, 26(1):1-9 (2005).
Peters et al., "30-50 Fold enrichment of hematopoietic progenitors directly from whole bone marrow in a single density centrifugation step", *Blood*, 98(11 Part 1):657A (2001).
Peters et al., "Extensive enrichment of hematopoietic progenitors from mobilized peripheral blood in a single centrifugation step", *Blood*, 96(11 Part 2)323B (2000).
Schneider et al., "In vitro and in vivo properties of a dimeric bispecific single-chain antibody IgG-fusion protein for depletion of CCR2+ target cells in mice", *Eur. J. Immunol.*, 35(3):987-995 (2005).
van Spriel et al., "Immunotherapeutic perspective for bispecific antibodies", *Immunol. Today*, 21(8):391-397 (2000).
Wognum et al., "Isolation of hematopoietic progenitor cells and mature cell subsets from rhesus monkey bone marrow and peripheral blood by negative selection", *Blood*, 98(11 Part 2):340B (2001).

* cited by examiner

*Primary Examiner* — Lynn Bristol
(74) *Attorney, Agent, or Firm* — DLA Piper LLP (US)

(57) ABSTRACT

The present invention relates to the treatment of immune system abnormalities that can be found in lethal human cancers and also in the progressive Human Immunodeficiency Virus Type 1 (HIV-1) infections and provides medicaments to correct abnormalities in a subject with cancer or HIV-1-infected subjects, in order to allow the immune system to fight the cancer or HIV-1 infections. The present invention also discloses multivalent polypeptides which specifically bind to and enable destruction and/or inactivation of immune cells that have CD11b and CD3 on their surface, therefore dissipating the deleterious effects of the $CD11b^+T$ cells.

7 Claims, 4 Drawing Sheets

1. Elevated absolute numbers of T cells in blood
    a. Most often linked to expansion of CD8+ T cells
    b. Inversion of CD4+/CD8+ T-cell ratio
2. Monoclonal or oligoclonal expansion of T cells primarily within the CD8+ T-cell subset
3. Increased proportion of CD45RO-expressing T-cells
4. Reduced expression of CD28 among T-cells, more reduced among CD8+ T-cells
5. Impaired up-regulation of CD154 (CD40 ligand) on CD4+ T cells after CD3 ligation.
6. Reduced lymphocyte proliferation in response to PHA.
7. Reduced lymphocyte proliferation in response to anti-CD3.

FIG. 2

Most often reported to be observed in cases of advanced-stage cancer arising in lung, colon, or breast. Also seen in malignant gliomaand leukemias.

1. Diminished skin test reactions to "recall" antigens
        a. Reduced induction of DNCB reactivity 2. Reduced in-vitro lymphocyte proliferation
        a. In response to "recall" antigens
        b. In response to phytohemagglutinin (PHA)
        c. In response to allogeneic stimuli These reactions are primarily dependent on normal T-cell function.

FIG. 3

BI-SPECIFIC MONOCLONAL ANTIBODY (SPECIFIC FOR BOTH CD3 AND CD11B) THERAPEUTIC DRUG

CROSS REFERENCE TO RELATED APPLICATION(S)

This application is a divisional and claims the benefit of priority under 35 U.S.C. §120 of U.S. patent application Ser. No. 11/821,127, filed Jun. 22, 2007, currently pending, which claims the benefit of priority under 35 U.S.C. §119(e) of U.S. Provisional Application No. 60/834,816, filed Jul. 29, 2006, the contents of which is incorporated herein by reference in its entirety.

BACKGROUND OF THE INVENTION

1. Field of the Invention

The invention relates generally to immunotherapy and, more specifically, to multivalent polypeptides directed to CD3 and CD11b cell surface markers, which markers are present on a subpopulation of immunosuppressing T cells, for therapeutic and diagnostic and prognostic use in cancer and infectious disorders.

2. Background Information

Patients with Chronic Lymphocytic Leukemia (CLL), usually a "B" cell cancer, commonly have abnormally large populations of certain kinds of non-cancerous "T" cells in the blood which have many CD11b molecules on their surface. Similarly, patients with progressive debilitating HIV-1 infections also have abnormally large populations of T cells with CD11b molecules on their surface, which normally comprise only a small percentage of the T cells in the blood of healthy people.

Evidence indicates that these T cells with CD11b on their surface (i.e., "CD11b$^+$") can interfere with or suppress the body's immune responses, and thus may have deleterious effects on one's ability to fight off cancer or HIV-1 infection. It appears that many types of human cancer and HIV-1 infection may elicit increased production of these CD11b$^+$T cells as a way of evading the immune response of the host.

SUMMARY OF THE INVENTION

The present invention relates to the treatment of immune system abnormalities that can be found in lethal human cancers and also in the progressive Human Immunodeficiency Virus Type 1 (HIV-1) infections. Specifically, the present invention provides medicaments to correct abnormalities in a subject with cancer or who is HIV-1-infected, in order to allow the immune system to better fight cancer or HIV-1 infections.

The present invention relates to multivalent polypeptides which specifically bind to and enable destruction and/or inactivation of immune cells that have CD11b and CD3 on their surface, therefore dissipating the deleterious effects of the CD11b$^+$T cells.

In one embodiment, an isolated multivalent polypeptide which specifically binds to CD3 and CD11b surface markers is disclosed.

In one aspect, the antibody is a bispecific, trispecific, tetravalent, hexavalent, octavalent, or decavalent antibody. In another aspect, the multivalent polypeptide is conjugated to a cytotoxic agent.

In another embodiment, a method for the treatment of an immunological disorder in a subject is disclosed, including administering to the subject, in an amount effective for the treatment, a pharmaceutical composition comprising (a) at least one multivalent polypeptide that (i) immunospecifically binds CD3 and CD11b surface markers and (ii) exerts a cytostatic or cytotoxic effect on a subpopulation of T-cell; and (b) a pharmaceutically acceptable carrier. In one aspect, the treatment may be in vitro, ex vivo, or by administration of the multivalent polypeptide intra- or peritumorally, where intra- or peritumoral administration induces infiltration by immunoeffector cells.

In one aspect, the immunological disorder includes, but is not limited to, cancer, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuromas, intestinal ganglioneuromas, hyperplastic corneal nerve tumor, Wilm's tumor, seminoma, ovarian tumor, cervical dysplasia and in situ carcinoma, neuroblastoma, retinoblastoma, soft tissue sarcoma, malignant carcinoid, topical skin lesion, rhabdomyosarcoma, Kaposi's sarcoma, osteogenic and other sarcoma, malignant hypercalcemia, renal cell tumor, adenocarcinoma, leukemias, lymphomas, malignant melanomas, epidermoid carcinomas, and other carcinomas and sarcomas.

In a related aspect, the cancer is chronic lymphocytic leukemia (CLL).

In another aspect, the immunological disorder is a viral infection, where the viral infection includes, but is not limited to, Epstein-Barr virus, human immunodeficiency virus, human T leukemia virus, hepatitis B virus, or measles virus.

In one embodiment, a kit is disclosed, including a multivalent polypeptide which specifically binds to CD3 and CD11b surface markers, a label, and instruction for using the multivalent polypeptide.

In another embodiment, a method for diagnosing an immunological disorder characterized by an increase in a circulating subpopulation of T cells bearing CD3 and CD11b cell surface markers is disclosed, including contacting a biological sample with a multivalent polypeptide which specifically binds to CD3 and CD11b surface markers and detecting binding. In one aspect, the detecting step comprises an immunoassay.

In another aspect, detecting of cells is by multicolor flow immunocytometry, fluorescence activated cell sorting (FACS), magnetic activated cell sorting (MACS), or digital image microscopy.

In one embodiment, a method of isolating a T cell subpopulation from a sample is disclosed, where the T cell subpopulation suppresses the immune response, including contacting the sample with a multivalent polypeptide which specifically binds to CD3 and CD11b surface markers under conditions suitable for the formation of an antibody-T cell complex, isolating a population of CD3$^+$/CD11b$^+$T cells from the sample, and substantially separating the isolated cells.

In a related aspect, the cells are substantially separated by a method including but not limited to, fluorescence activated cell sorting (FACS) and magnetic activated cell sorting (MACS).

BRIEF DESCRIPTION OF THE DRAWINGS

FIG. 2 shows a list of T lymphocyte abnormalities commonly found in untreated cases of B-cell CLL.

FIG. 3 shows a list of acquired immune defects in patients with cancer.

DETAILED DESCRIPTION OF THE INVENTION

Figure 1:
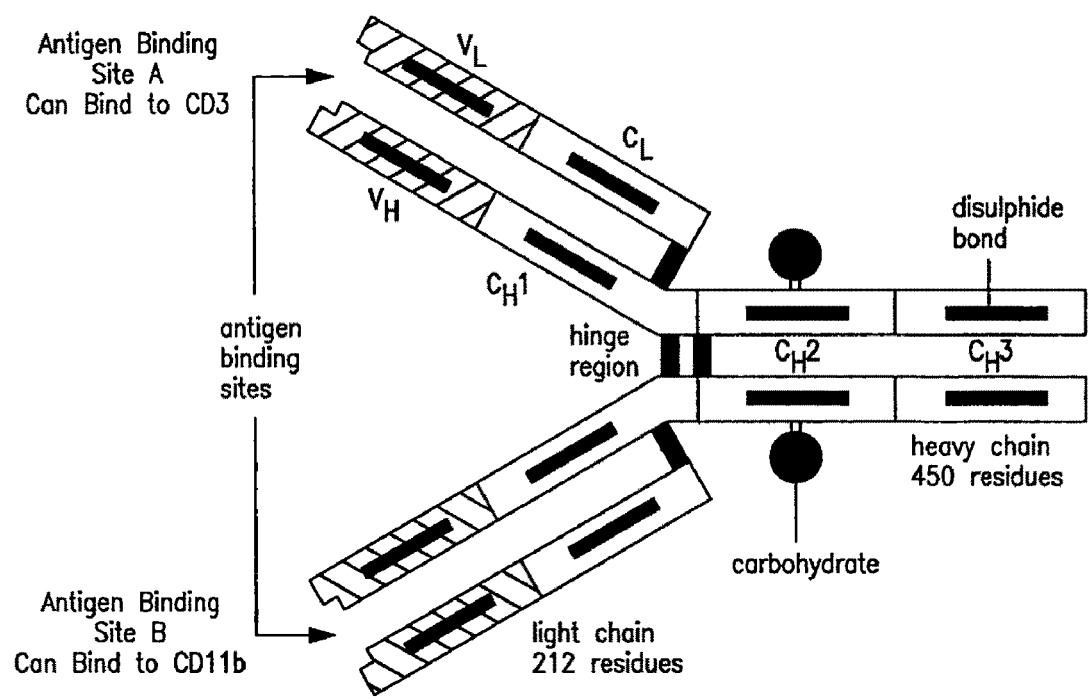
FIG. 1 shows an illustration of an example bispecific antibody of the present invention.

Before the present composition, methods, and isolation methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a polypeptide" includes one or more polypeptides, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

"Bispecific antibody" and "bispecific antibodies," also known as bifunctional antibodies, intends antibodies that recognize two different antigens by virtue of possessing at least one first antigen combining site specific for a first antigen or hapten, and at least one second antigen combining site specific for a second antigen or hapten. Such antibodies can be produced by recombinant DNA methods or include, but are not limited to, antibodies produced chemically by methods known in the art. Chemically created bispecific antibodies that have been reduced and reformed so as to retain their bivalent characteristics and antibodies that have been chemically coupled so that they have at least two antigen recognition sites for each antigen. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

In one embodiment, an isolated multivalent polypeptide which specifically binds to CD3 and CD11b surface markers is disclosed.

In one aspect, the antibody is a bispecific antibody. In another aspect, the multivalent polypeptide is conjugated to a cytotoxic agent.

As used herein the term "effector cell population" intends a cell population which comprises at least one T cell. An effector cell population can be obtained from a starting cell population from which antigen-specific T cells are enriched.

The terms "cell," and "cells," and "cell population," used interchangeably, intend one or more mammalian cells. The term includes progeny of a cell or cell population. Those skilled in the art will recognize that "cells" include progeny of a single cell, and the progeny can not necessarily be completely identical (in morphology or of total DNA complement) to the original parent cell due to natural, accidental, or deliberate mutation and/or change.

The terms "T lymphocyte," "T cell,". "T cells," and "T cell population," used interchangeably, intends a cell or cells which display on their surface one or more antigens characteristic of T cells, such as, for example, CD3 and CD11b. The term includes progeny of a T cell or T cell population. A "T lymphocyte" or "T cell" is a cell which expresses CD3 on its cell surface and a T cell antigen receptor (TCR) capable of recognizing antigen when displayed on the surface of autologous cells, or any antigen-presenting matrix, together with one or more MHC molecules or, one or more non-classical MHC molecules. The term "T cells" as used herein denotes any T cells known in the art, for instance, lymphocytes that are phenotypically CD3$^+$, i.e., express CD3 on the cell surface, typically detected using an anti-CD3 monoclonal antibody in combination with a suitable labeling technique. The T cells enriched by the methods of this invention are generally CD3$^+$. The T cells enriched by the methods of this invention are also positive for CD11b.

In one embodiment, a method of isolating a T cell subpopulation from a sample is disclosed, where the T cell subpopulation suppresses the immune response, including contacting the sample with a multivalent polypeptide which specifically binds to CD3 and CD11b surface markers under conditions suitable for the formation of an antibody-T cell complex, isolating a population of CD3$^+$/CD11b$^+$T cells from the sample, and substantially separating the isolated cells.

The term "substantially enriched" or "substantially isolated" as used herein, indicates that a cell population is at least about 50-fold, more preferably at least about 500-fold, and even more preferably at least about 5000-fold or more enriched from an original mixed cell population comprising the desired cell population.

A "subject" is a vertebrate, preferably a mammal, more preferably a human. Mammals include, but are not limited to, humans, farm animals, sport animals, and pets.

An "effective amount" is an amount sufficient to effect beneficial or desired clinical results. An effective amount can be administered in one or more administrations. For purposes of this invention, an effective amount of multivalent polypeptide is an amount that is sufficient to diagnose, palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

In another embodiment, a method for the treatment of an immunological disorder in a subject is disclosed, including administering to the subject, in an amount effective for the treatment, a pharmaceutical composition including (a) at least one multivalent polypeptide that (i) immunospecifically binds CD3 and CD11b surface markers and (ii) exerts a cytostatic or cytotoxic effect on a subpopulation of T-cell; and (b) a pharmaceutically acceptable carrier.

In one aspect, the immunological disorder includes, but is not limited to, cancer, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuromas, intestinal ganglioneuromas, hyperplastic corneal nerve tumor, Wilm's tumor, seminoma, ovarian tumor, cervical dysplasia and in situ carcinoma, neuroblastoma, retinoblastoma, soft tissue sarcoma, malignant carcinoid, topical skin lesion, rhabdomyosarcoma, Kaposi's sarcoma, osteogenic and other sarcoma, malignant hypercalcemia, renal cell tumor, adenocarcinoma, leukemias, lymphomas, malignant melanomas, epidermoid carcinomas, and other carcinomas and sarcomas.

In a related aspect, the cancer is chronic lymphocytic leukemia (CLL).

In another aspect, the immunological disorder is a viral infection, where the viral infection includes, but is not limited to Epstein-Barr virus, human immunodeficiency virus, human T leukemia virus, hepatitis B virus, or measles virus.

The effector cell population can be subjected to one or more separation protocols based on the expression of cell surface markers. For example, the cells can be subjected to positive selection on the basis of expression of one or more cell surface polypeptides, including, but not limited to, "cluster of differentiation" cell surface markers such as CD2, CD3, CD4, CD8, TCR, CD45, CD45RO, CD45RA, CD11b, CD26, CD27, CD28, CD29, CD30, CD31, CD40L; other markers associated with lymphocyte activation, such as the lymphocyte activation gene 3 product (LAG3), signaling lymphocyte activation molecule (SLAM), T1/ST2; chemokine receptors such as CCR3, CCR4, CXCR3, CCR5, homing receptors such as CD62L, CD44, CLA, CD146, a4(37, aE37; activation markers such as CD25, CD69 and OX40; and lipoglycans presented by CD1. The effector cell population can be subjected to negative selection for depletion of non-T cells and/or particular T cell subsets. Negative selection can be performed on the basis of cell surface expression of a variety of molecules, including, but not limited to, B cell markers such as CD19, and CD20; monocyte marker CD14; the NK cell marker CD56.

Generally, antibodies suitable for practicing the methods of the present invention immunospecifically bind CD3 and CD11b. Antibodies suitable for practicing the methods of the invention are preferably monoclonal and multivalent, and may be human, humanized or chimeric antibodies, comprising single chain antibodies, Fab fragments, F(ab') fragments, fragments produced by a Fab expression library, and/or binding fragments of any of the above. The term "antibody," as used herein, refers to immunoglobulin molecules and immunologically active portions of immunoglobulin molecules, i.e., molecules that contain at least two antigen binding sites that immunospecifically bind CD3 and CD11b. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In certain embodiments of the invention, the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, $CH_1$, $CH_2$, $CH_3$ and CL domains. Also included in the invention are antigen-binding fragments also comprising any combination of variable region(s) with a hinge region, $CH_1$, $CH_2$, $CH_3$ and CL domains. Preferably, the antibodies are human, murine (e.g., mouse and rat), donkey, sheep, rabbit, goal, guinea pig, camelid, horse, or chicken. As used herein, 'human' antibodies include antibodies having the amino acid sequence of a human immunoglobulin and include antibodies isolated from human immunoglobulin libraries, from human B cells, or from animals transgenic for one or more human immunoglobulins.

In one embodiment, the antibody is a bispecific antibody as illustrated in FIG. 1. In one aspect, the antibody may comprise human IgG1, with a binding site A (top $V_L/V_H$ region), capable of binding to a CD3 molecule, and binding site B (lower corresponding region) capable of binding to a CD11b molecule.

The antibodies suitable for practicing the methods of the present invention may be bispecific, trispecific or of greater multispecificity. Further, the antibodies of the present invention have low risk of toxicity against granulocyte (neutrophil), NK cells, and CD4$^+$ cells as bystander cells.

Multivalent antibodies have binding specificities for at least two different antigens. While such molecules normally will only bind two antigens (i.e., bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoet-hylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J Exp. Med,* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kos-telny et al., *J. Immunol,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

Multivalent antibodies may be specific for different epitopes of CD3 and CD11b, including, for example, that the multivalent antibodies may bind to one or more of the epitopes present on either CD3 or CD11b. Multivalent antibodies, including bispecific and trispecific antibodies, useful for practicing the present invention are antibodies that immunospecifically bind to both CD3 and CD11b, and may bind one or more additional lymphocyte surface receptors or receptor complexes, such as an immunoglobulin gene superfamily member, a TNF receptor superfamily member, an integrin, a cytokine receptor, a chemokine receptor, a major histocompatibility protein, a lectin (C-type, S-type, or I-type), or a complement control protein.

Antibodies useful in the present methods may be described or specified in terms of the particular CDRs they comprise. The invention encompasses the use of an antibody or derivative thereof comprising a heavy or light chain variable domain, said variable domain comprising (a) a set of three CDRs, and (b) a set of four framework regions, and in which said antibody or derivative thereof immunospecifically binds CD3 and CD11b.

Within the context of the present invention, antibodies are understood to include monoclonal antibodies and polyclonal antibodies, antibody fragments (e.g., Fab and $F(ab')_2$), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^7$ $M^{-1}$. Additionally, antibodies that may be used in the methods of the present invention may also be described or specified in terms of their binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{--13}$ M, $10^{-13}$ M, $5\times10^{-14}$ M, $10^{-14}$ M, $5\times10^{-15}$ M, or $10^{-15}$ M.

Antibodies can be fragmented using conventional techniques and the fragments screened for utility in the same manner as described above for the whole antibodies. For example, $F(ab')_2$ fragments can be generated by treating antibody with pepsin. The resulting $F(ab')_2$ fragment can be treated to reduce disulfide bridges to produce Fab' fragments The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio) propionate (SPDP) combine exposed amino groups of antibodies and Fab fragments, regardless of class or isotype (Van Dijk et al., 1989).

The antibodies of the invention, i.e., antibodies that are useful for treating immunological disorders, include derivatives that are modified, i.e., by the covalent attachment of any type of molecule to the antibody such that covalent attachment does not prevent the antibody from binding to CD3/CD11b. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of turicamycin, etc. Additionally, the derivative may contain one or more non-classical amino acids.

The antibodies that may be used in the treatment of immunological disorders may be generated by any suitable method known in the art. Polyclonal antibodies to CD3/CD11b can be produced by various procedures well known in the art. For example, CD3/CD11b can be administered to various host animals including, but not limited to, rabbits, mice, rats, etc. to induce the production of sera containing polyclonal antibodies specific for the protein. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammer-ling, et al., in: Monoclonal Antibodies and T-Cell Hybrido-mas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with CD3/CD11b or a cell expressing CD3/CD11b or a fragment or derivative thereof. Once an immune response is detected, e.g., antibodies specific for CD3/CD11b are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding CD3/CD11b and exerting a cytotoxic or cytostatic effect on activated lymphocytes. Ascites fluid, which generally contains high levels of antibodies, can be generated by injecting mice with positive hybridoma clones.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH$_1$ domain of the heavy chain.

For example, antibodies useful in the methods of the present invention can also be generated using various phage display methods known in the art. In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g. human or murine). In phage display methods, functional antibody domains are displayed on the surface of phage particles which carry the nucleic acid sequences encoding them. In particular, DNA sequences encoding V$_H$ and V$_L$ domains are amplified from animal cDNA libraries (e.g., human or murine cDNA libraries of lymphoid tissues). The DNA encoding the V$_H$ and V$_L$ domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 binding domains expressed from phage with Fab, Fv or disulfide stabilized Fv antibody domains recombinantly fused to either the phage gene III or gene VIII protein. Phage expressing an antigen binding domain that binds to CD3/CD11b or portions thereof can be selected or identified with antigen e.g., using labeled antigen or antigen bound or captured to a solid surface or bead. Examples of phage display methods that can be used to make the antibodies of the present invention include those disclosed in Brinkman et al, 1995, J. Immunol. Methods 182:41-50; Ames et al., 1995, J. Immunol. Methods 184:177-186; Kettleborough et al, 1994, Eur. J. Immunol. 24:952-958; Persic et al., 1997, Gene 187: 9-18; Burton et al., 1994, Advances in Immunology, 191-280; PCT Application No. PCT/GB91/01134; PCT Publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al, BioTechniques 1992, 12(6):864-869; and Sawai et al, 1995, AJRI 34:26-34; and Better et al., 1988, Science 240:1041-1043.

Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; and Skerra et al., 1988, Science 240:1038-1040. For some uses, including in vivo use of antibodies in humans and in vitro proliferation or cytotoxicity assays, it is preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229: 1202; Oi et al, 1986, Bio-Techniques 4:214; Gillies et al., 1989, J. Immunol. Methods 125:191-202; U.S. Pat. Nos. 5,807,715; 4,816,567; and 4,816,397. Humanized antibodies are antibody, molecules from non-human species antibodies that bind the desired antigen having one or more CDRs from the non-human species and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology, 1991, 28(4/5):489-498; Studnicka et al., 1994, Protein Engineering 7(6):805-814; Roguska. et al, 1994, PNAS 91:969-973), and chain shuffling (U.S. Pat. No. 5,565,332).

Completely human antibodies are particularly desirable for the therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Human antibodies can also be produced using transgenic mice which express human immunoglobulin genes. For example, the human heavy and light chain immunoglobulin gene complexes may be introduced randomly or by homologous recombination into mouse embryonic stem cells. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of CD3 and CD 11b. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Freemont, Calif.) and Medarex (Princeton, N.J.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1994, Bio/technology 12:899-903).

Further, antibodies to CD3/CD11b can, in turn, be utilized to generate anti-idiotype antibodies that "mimic" proteins of the invention using techniques well known to those skilled in the art. (See, e.g. Greenspan & Bona, 1989, FASEB J. 7(5): 437-444; and Nissinoff. 1991, J. Immunol. 147(8):2429-243S). Fab fragments of such anti-idiotypes can be used in therapeutic regimens to elicit an individual's own immune response against CD3/CD11b present on activated lymphocytes.

Aside from the antibodies specifically identified above, the skilled practitioner could generate polyclonal antibodies directed against an antigen of interest.

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soy-bean trypsin inhibitor using a bifunctional or derivatizing agent, for example, maleimidobenzoyl sulfosuccinimide ester (conjugation through cysteine residues), N-hydroxy-ysuccinimide (through lysine residues), glutaraldehyde, succinic anhydride, $SOCl_2$, or $R^1N = C = NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-1 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552-554 (1990). Clackson et al. *Nature*, 352:624-628 (1991) and Marks et al, *J. Mol. Biol*, 222:581-597 (1991) describe the isolation of murine and human antibodies, respectively, using phage libraries. Subsequent publications describe the production of high affinity (nM range) human antibodies by chain shuffling (Marks et al, *Bio/Technology*, 10:779-783 (1992)), as well as combinatorial infection a in vivo recombination as a strategy for constructing very large phage libraries (Waterhouse et al., *Nuc. Acids. Res.*, 21:2265-2266 (1993)). Thus, these techniques are viable alternatives to traditional hybridoma techniques for isolation of monoclonal antibodies.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Immunoadhesins may also be used according to the methods of the present invention. The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $CH_2$ and $CH_3$ domains of the constant region of an immunoglobulin heavy chain. Fusions are also made to the C-terminus of the Fc portion of a constant domain, or immediately N-terminal to the $CH_1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin Gj (IgGj). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $CH_2$ and $CH_3$ or (b) the $CH_1$, hinge, $CH_2$ and $CH_3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multivalent form in serum. In the case of multimer, each of the four units may be the same or different.

Various exemplary assembled immunoadhesins within the scope herein are schematically diagrammed below:
(a) $AC_L$-$AC_L$;
(b) $AC_H$-($AC_H$, $AC_L$-$AC_H$, $AC_L$-$V_H C_H$, or $V_L C_L$-$AC_H$);

(c) $AC_L$-$AC_{H'}$-($AC_L$-$AC_{H3}$, $AC_L$-$V_HC_{H'}$, $V_LC_L$-$AC_{H'}$, or $V_LC_L$-$V_HC_H$)

(d) $AC_L$-$V_HC_{H'}$-($AC_{H'}$, or $AC_L$-$V_HC_H$ or $V_LC_L$-$AC_H$);

(e) $V_LC_L$-$AC_{H'}$-($AC_L$-$V_HC_H$, or $V_LC_L$-$AC_H$); and (f) $(A-Y)_n$-$(V_LC_L$-$V_HC_H)_2$, wherein each A represents identical or different adhesin amino acid sequences:

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $CH_2$ domain, or between the $CH_2$ and $CH_3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immuno-globulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., Cell 61:1303-1313 (1990); and Stamenkovic et al., Cell 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

Analysis of the cell population and cell sorting based upon the presence of the label can be accomplished by a number of techniques known in the art. Cells can be analyzed or sorted by, for example, flow cytometry or FACS. These techniques allow the analysis and sorting according to one or more parameters of the cells. Usually one or multiple secretion parameters can be analyzed simultaneously in combination with other measurable parameters of the cell, including, but not limited to, cell type, cell surface markers, DNA content, etc. The data can be analyzed and cells sorted using any formula or combination of the measured parameters. Cell sorting and cell analysis methods are known in the art and are described in, for example, *The Handbook of Experimental Immunology*, Volumes 1 to 4, (D. N. Weir, editor); *Flow Cytometry Cell Sorting* (A. Radbruch, editor, Springer Verlag, 1992); and *Cell Separation Methods and Applications* (D. Recktenwald and A. Radbruch, eds., 1997) Marcel Dekker, Inc. N.Y. Cells can also be analyzed using microscopy techniques including, for example, laser scanning microscopy, fluorescence microscopy; techniques such as these can also be used in combination with image analysis systems. Other methods for cell sorting include, for example, panning and separation using affinity techniques, including those techniques using solid supports such as plates, beads and columns.

Some methods for cell sorting utilize magnetic separations, and some of these methods utilize magnetic beads. Different magnetic beads are available from a number of sources, including for example, Dynal (Norway), Advanced Magnetics (Cambridge, Mass., U.S.A.), Immun-con (Philadelphia, U.S.A.), Immunotec (Marseilles, France), and Miltenyi Bio tec GmbH (Germany).

Preferred magnetic labeling methods include colloidal superparamagnetic particles in a size range of 5 to 200 nm, preferably in a size of 10 to 100 nm. These magnetic particles allow a quantitative magnetic labeling of cells, thus the amount of coupled magnetic label is proportional to the amount of bound product, and the magnetic separation methods are sensitive to different amounts of product secretion. Colloidal particles with various specificities are known in the art, and are available, for example, through Miltenyi Biotec GmbH. The use of immunospecific fluorescent or magnetic liposomes can also be used for quantitative labeling of captured product. In these cases, the liposomes contain magnetic material and/or fluorescent dyes conjugated with antibody on their surfaces, and magnetic separation is used to allow optimal separation between nonproducing, low producing, and high producing cells.

The magnetic separation can be accomplished with high efficiency by combining a second force to the attractive magnetic force, causing a separation based upon the different strengths of the two opposed forces. Typical opposed forces are, for example, forces induced by magnetic fluids mixed in the separation medium in the magnetic separation chamber, gravity, and viscous forces induced by flow speed of medium relative to the cell. Any magnetic separation method, preferably magnetic separation methods allowing quantitative separation will be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique the product is labeled by attaching it to a magnetic particle. The attachment is generally through association of the product with a label moiety which is conjugated to a coating on the magnetic particle which provides a functional group for the conjugation. The captured product thus coupled to a magnetic "label", is suspended in a fluid which is then applied to the chamber. In the presence of a magnetic gradient supplied across the chamber, the magnetically labeled target cell is retained in the chamber; if the chamber contains a matrix, it becomes associated with the matrix. Cells which do not have or have only a low amount of magnetic labels pass through the chamber.

The retained cells can then be eluted by changing the strength of, or by eliminating, the magnetic field or by introducing a magnetic fluid. The selectivity for a captured product is supplied by the label moiety conjugated either directly or indirectly to the magnetic particle or by using a primary antibody and a magnetic particle recognizing the primary antibody. The chamber across which the magnetic field is applied is often provided with a matrix of a material of suitable magnetic susceptibility to induce a high magnetic field gradient locally in the camber in volumes close to the surface of the matrix. This permits the retention of fairly weakly magnetized particles. Publications describing a variety of HGMS systems are known in the art, and include, for example, U.S. Pat. Nos. 4,452,773, 4,230,685, PCT application WO85/04330, U.S. Pat. No. 4,770,183, and PCT/EP89/01602; systems are also described in U.S. Pat. Nos. 5,411,863; 5,543,289; 5,385,707; and 5,693,539.

In addition, in other embodiments the processes include labeling the cells that contain the product captured by the capture moiety, if any. Other embodiments can also include analyzing the cell population to detect labeled cells, if any, and if desired, sorting the labeled cells, if any.

The present invention further provides diagnostic methods for detecting antigen-specific T cells. These include methods for analyzing a population of cells enriched for T cells to identify or enumerate antigen-specific T cells, as well as methods of determining a distribution of antigen-specific T cells.

Methods for analyzing a population of cells enriched in T cells to identify or enumerate antigen-specific T cells relative to other cells in the population, comprise the steps of labeling the cells by the methods of the present invention; labeling the cells and detecting the amount of label. Such methods are useful, for example, in determining the proportion of a cell population that is specific for a given antigen. The method can be used to provide information regarding the immune status of an individual, including assessing an immune response to allergens, a tumor or virus, or evaluating the proportion of cells in an individual that are self reactive so as to detect or monitor autoimmune diseases.

The present invention provides methods of treatment of a disease or condition related to a population of antigen-specific T cells, using the multivalent polypeptide of the invention.

Treatment methods include those in which an antigen-specific T cell population is identified, and in an individual; those in which a population of antigen-specific T cells is identified and diminished/reduced in vitro before the T-cell population is reintroduced into an individual; those in which a population of antigen-specific T cells is identified and eliminated from a population of cells to be introduced into an individual; ex vivo genetic modification prior to administration; and selection of antigen-specific T cells according to CD3/CD11b expression.

In one embodiment, a kit is disclosed, including a multivalent polypeptide which specifically binds to CD3 and CD11b surface markers, a label, and instruction for using the multivalent polypeptide. In one aspect, the components of the kit may be used to predict the effectiveness of the treatment of a subject administered the multivalent polypeptide of the present invention, where the subject has an immunological disorder.

The kit can also be formulated to include the following: all the reagents are preferably placed in a single vial to which the cells are added. At least one antibody which is bispecific for a particular cell surface structure and, optionally, at least one label moiety Optionally, the kit can include physiologically acceptable buffer. Such buffers are known in the art and include, but are not limited to, PBS with and without BSA, isotonic saline, cell culture media and any special medium required by the particular cell type. Buffers can be used that reduce cross-labeling and increase the local product concentration around the cells. Buffers can include agents for increasing viscosity or decreasing permeability. Suitable agents are described herein. The viscosity of the medium can be reduced before analysis by any method known in the art including, but not limited to, dissolution in a physiologically acceptable buffer, dissolving heat, EDTA, and enzymes. In the absence of added medium, cells already suspended in a medium can be directly added to the vial. Suitable cell suspensions include but are not limited to cell lines and biological samples. Biological samples include, but are not limited to, blood, urine and plasma.

Additional label moieties such as antibodies (magnetically or fluorescently labeled) can also be present, including, but not limited to anti-cell surface marker antibodies to identify cell types, propidium iodide to label dead cells, and magnetic beads to label certain cell types.

In one embodiment, all materials can be placed in a single container such as a vial and the cell sample added. The contents are incubated to allow secretion of a product and subsequent capture of the product and binding of the label moiety to the product. The cells which have secreted and bound product can then be separated and/or analyzed based on the presence, absence or amount of the captured product. Separation can be done by any of the methods known in the art, including, but not limited to, simple dilution, erythrocyte lysis, centrifugation-washing step, magnetic separation, FACS and Ficoll separation. The analysis of the cells can be performed by a variety of methods, including, but not limited to, FACS, image analysis, cytological labeling, and immunoassay.

The pharmaceutical compositions of the present invention may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable (pharmaceutically acceptable) diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In some aspects, double therapeutic agents may be used comprising multivalent polypeptides which deliver toxins or radionuclides, including, but not limited to, $P^{32}$, $P^{33}$, $Sc^{47}$, $Cu^{64}$, $Cu^{67}$, $As^{77}$, $Y^{90}$, $PH^{105}$, $Pd^{109}$, $Ag^{111}$, $I^{125}$, $Pr^{143}$, $Sm^{153}$, $Tb^{161}$, $Lu^{177}$, $Re^{186}$, $Re^{188}$, $Re^{189}$, $Ir^{194}$, $Au^{199}$, $Pb^{212}$, and $Bi^{213}$.

In other aspects, the chemotherapeutic agents may be used including, but not limited to, adriamycin, doxorubicin, epirubicin, 5-fluorouracil, cytosine arabinoside, cyclophosphamide, thiotepa, busulfan, cytoxin, paclitaxel, doxetaxel, toxotere, methotrexate, cisplatin, melphalan, vinblastine, bleomycin, etoposide, ifosfamide, mitomycin C, fludarabine, cladaribine, mitoxantrone, vincristine, vinorelbine, carboplatin, teniposide, daunomycin, caminomycin, aminopterin, dactinomycin, mitomycins, esperamicins, 5-FU, 6-thioguanine, 6-mercaptopurine, actinomycin D, VP-16, chlorambucil, melphalan, or a combination thereof.

In one aspect, a toxin may be used including, but not limited to, diphtheria A chain, a nonbinding active fragment of diphtheria toxin, a nonbinding active fragment of cholera toxin, a nonbinding active fragment of botulin toxin, *Pseudomonas aeruginosa* exotoxin A chain, ricin A chain, abrin A chain, modeccin A chain, alpha-sarcin, *Aleurites fordii* proteins, dianthin proteins, *Phytolaca americana* proteins PAPI, PAPII, PAP-S, *Momordica charantia* inhibitor, curcin, crotin, *Sapaonaria officinalis* inhibitor, gelonin, saporin, mitogellin, restrictocin, phenomycin, enomycin, tricothecenes, calicheamicins, maytansinoids, palytoxin, CC1065, or a combination thereof. Further, such toxin may also possess a radioactive moiety, including, but not limited to those recited above.

It will be understood, however, that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following examples are intended to illustrate but not limit the invention.

EXAMPLES

Generation of Single Chain Antibody Fragments from Monoclonal Antibodies to CD3 and to CD11b.

The techniques described in this Example can be used to generate a single chain antibody fragment (ScFv) of either the anti-CD3 or anti-CD11b monoclonal antibodies.

Both the $V_H$ and $V_L$ region of the antibodies are amplified by PCR, followed by a second assembly PCR to connect both regions. Four primers can be designed. The first contains restriction site for cloning purposes followed by a degenerated sequence annealing to the 5' $V_H$ region. The second contains a degenerate sequence for the 3' part of the $V_H$ region followed by a sequence encoding a $((Gly)_4Ser)_3$ (SEQ ID NO: 1) linker and the 5' part of the $V_L$ regions. The third is a degenerated primer having homology with the 5' part of the $V_L$ region, while the last primer contains an appropriate restriction site and anneals to the 3' part of the $V_L$ region.

As a template for this PCR reaction, one can use a plasmid containing the $V_H$ or $V_L$ regions of the antibody of interest. The cDNA obtained in this PCR step is gel purified and used in an assembly PCR resulting in the linkage of the V region through the $((Gly)_4Ser)_3$ (SEQ ID NO: 1) linker. Subsequently the single chain construct obtained is digested with the appropriate restriction enzymes, followed by ligation into an expression vector. The ligation is transformed in DH5a and plated on LB plates. By sequencing of several clones, a correct ScFv clone is found.

Construction of Bispecific Diabody Molecules Capable of Binding to CD4 and CD11b.

Bispecific bivalent molecules can be generated by shortening the flexible linker sequence in the anti-CD3 ScFv and in the anti-CD11b ScFv, from fifteen residues to five $((Gly)_4Ser)_3$ (SEQ ID NO: 1) and by cross-pairing the variable heavy and light chain domains from the two single chain Fv fragments with the different antigen recognition. The construction is preferably performed in three steps. The light chain variable fragments are exchanged in the ScFv constructs from an anti-CD3 ScFv and an anti-CD11b ScFv by using restriction enzyme sites located in the 5'-end and just outside the 3'-part of the light chain variable gene. In the following step, the 15-residue linker of the chimeric construct $V_H$-a CD3/15AA-linker/$V_L$-a CD11b is replaced by the 5 residue linker $((Gly)_4Ser)_3$ (SEQ ID NO: 1) by using sites located in the 3'-part of $V_H$ and the 5'-part of $V_L$. Finally, a chimeric cassette is combined in an appropriate vector, containing a bi-cistronic expression cassette. A diabody-producing clone containing both ScFv-cassettes is identified and used for expression of the recombinant diabody molecule.

Example 1

Evidence for Low Risk of Cellular Toxicity for Bystander Cells

Subjects

Normal subjects and a consecutive group of consenting patients at Scripps Clinic and Scripps Memorial Hospital-LaJolla, who were diagnosed with B-CLL were recruited according to an Institutional Review Board [IRB]-approved protocol. Blood specimens were analyzed in a blinded fashion. For leukemic patients, extensive immunophenotyping was done on each specimen to confirm the diagnosis of B-CLL.

Flow Cytometry

Flow cytometry was performed with FACScan, Ortho-Cytotron, or FACSCalibur instruments, used interchangeably based on availability at Esoterix Oncology. Whole blood preparations were stained and fixed prior to cytometry according to the manufacturer's instructions (Becton-Dickenson) with the exception that red blood cell (RBC) lysis was done with ammonium chloride-based reagent.

Cytometry Computer Software

Software capable of high resolution multidimensional data analysis was used (see, e.g., Bjork et al., Clin App Immunol Rev (2002) 2:141-154). The software has both manual and automated population analysis features, and results can be easily displayed and cross-checked with currently marketed software that generates 2-dimensional dot plots (e.g., such software for 2 dimensional dot plots may be obtained from Purdue University Cytometry Laboratory (PUCL) website, hosted by J. Paul Robinson, Director PUCL, Bindley Bioscience Center, Purdue University, West Lafayette, Ind.).

Experimental Data

Patients with B-cell CLL (B-CLL) have a virtual constellation of associated T cell disorders (FIG. 2) of unknown etiology. These impairments are similar to those found in blood mononuclear cells of untreated B-CLL cases, untreated GM cases, lung cancer cases, colon cancer cases, and breast cancer cases, including: impaired responses to recall antigens, and reduced lymphocyte proliferation reactions to allogenic stimuli and to mitogens such as phytohemagglutinin (PHA) (FIG. 3).

A cross sectional study of 23 cases of B-CLL, representing all Rai stages, revealed a high prevalence of expanded subsets of $CD3^+/CD11b^+$ cells among the $CD8^+$ T lymphocytes in the blood. Abnormally large subsets of these cells were found in 8 of 16 early state (Rai 0 or 1) and 5 of 7 advanced-stage (Rai 2 to 4) cases, some of whom were on chemotherapy at the time of blood drawing. Another trend discovered was the ratio of $CD28^+CD8^+T$ cells (Tc) to putative immune suppressor T cells (i.e., $CD3^+/CD11b^+T$ cells (Ts), or Tc/Ts, tended to be lower in B-CLL cases (mean 1.6, range 0.4-3.8) compared to normal subjects (mean 13, range 1.1-100).

Figure 4:
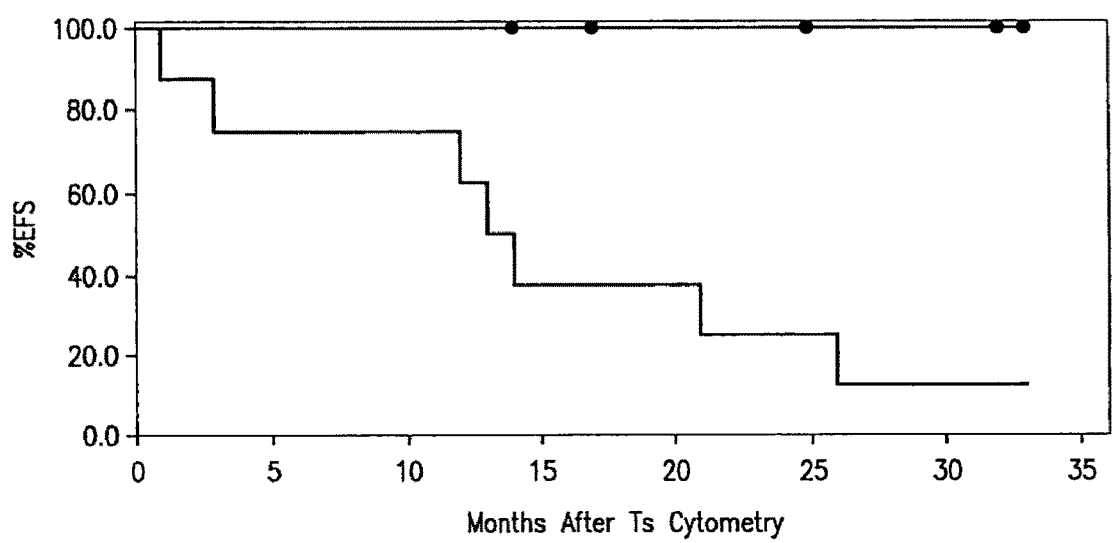
FIG. 4 shows a life-table analysis for two groups of patients, where one group has a T-cell count of 160 or less and the other group has a T-cell count of greater than 160.

In was observed that seven of the eight cases with abnormally high Ts counts (180 or greater) experienced a CLL-related event during the prospective study period (EFS=12.5%). The eighth case was 14 months post-research cytometry, and had no evidence of significant disease progression. In contrast, five of five cases with Ts counts of 160 or less have remained event free (EFS=100%). FIG. 4 illustrates a life-table analysis of the two groups, with median follow-up of 30 months, in which the difference in the probability of EFS is statistically significant (P=0.01). In essence, irrespective of any B-cell related parameter, the absolute count of putative Ts appeared to independently correlate with elements of disease progression in the early stages of these B-CLL cases.

Thirteen cases of B-CLL patients (samples were obtained from J. Moore, Philadelphia) were studied based on progression of their disease (the median medical follow-up of the updated data is 49 months after experimental cytometry and 60 months after diagnosis): among 6 cases which continue to have non-progressive disease, the mean absolute count of $CD11b^+/CD3^+$ T-cells was 161 (range 91-338, SD=89), while the corresponding absolute counts among 7 cases with progressive disease was 507 (range 180-932; SD=251). Alternatively, these cases could be divided into two groups based on absolute $CD11b^+/CD3^+$ counts: 8 cases had high counts (>2 SD above the mean for normal healthy controls) and 5 cases had normal counts. Although the age sex, Rai stage, and absolute lymphocyte counts were not significantly different in the two groups, there was a statistically significant difference in progression-free survival between the two groups: 7 of the 8 cases with high $CD11b^+/CD3^+$ T cell counts (180 or greater) had disease progression, while 5 of 5 with normal counts remain progression-free and asymptomatic (p=0.01).

A predominant majority of granulocytes (i.e., neutrophils) and their precursors express CD11b on the cell surface. Thus, any drug/agent targeting only the CD11b molecule will be expected to have significant "bystander" toxicity on the granulocyte cell lineage. Similarly, natural killer (NK) lymphocytes (i.e., $CD56^+$ lymphocytes) also express CD11b on their cell surface, and would also become "bystander" targets of a CD11b-focused therapeutic strategy. However, there is no consensus on whether a significant percentage of T-helper cells (i.e., $CD4^+$ cells) express CD11b.

TABLE 1

% of Neutrophils (Granulocytes) that Express
CD3 on their Surfaces: 65 Cases of CLL

| Case | % Expression |
| --- | --- |
| Case 1: C. B. | <1% |
| Case 2: M. A. | <1% |
| Case 3: R. E. | <1% |
| Case 4: M. M. | <1% |
| Case 5: J. W. | 9.50% |
| Case 6: H. G. | 7% |

In 4 cases of CLL, 1.3%, 4%, 6%, and 25% of NK cells express CD3 on their surface (see, Table 2).

TABLE 2

% of NK cells (CD 56+ lymphocytes) that
Express CD3 on Their Surfaces: 4 Cases of CLL.

| Case | % Expression |
| --- | --- |
| Case 1: J. G. | 1.30% |
| Case 2: G. B. | 4% |
| Case 3: H. S. | 6% |
| Case 4: B. H. | 25% |

In 10 cases of CLL, the percentage of T helper cells that co-express CD11b ranges from 2.5% to 17%, with a mean of 5.6%. This data shows that a small percent of $CD3^+$ and $CD11b^+$ cells are T-helper (i.e. $CD4^+$) cells, so that the percentage of CD11b+/$CD3^+$ lymphocytes is approximately the same as the percentage of $CD8^+/CD11b^+/CD3^+$ lymphocytes (see, Table 3).

TABLE 3

Summary of Flow Cytometry Data on Blood Lymphocytes Subsets in B-CLL Study Subjects*

| Cases | Normals | Lymphs (34 28-39) | $CD19^+$ 13 (11-16) | NK Cells 14 (10-19) | T Cells 72 (67-76) | T4/T8 1.2 (1.0-1.5) | $CD8^+$ $CD28^-$ (≦16) | $CD3^+$ $CD8^+$ $CD11b^+$ (≦16) | $CD8^+$ $CD56^+$ $CD11b^+$ (≦16) | $CD3^+$ $CD11b^+$ T4 |
| --- | --- | --- | --- | --- | --- | --- | --- | --- | --- | --- |
| 1 | M.S. | 37 | 24 | 3 | 12 | 1.50 | 55 | 45 | 14 | 6 |
| 2 | G.D. | 44 | 30 | 6 | 21 | 2.60 | 35 | 27 | 18 | 2.5 |
| 3 | D.G. | 64 | 43 | 9 | 20 | 0.57 | 76 | 24 | 3 | 6 |
| 4 | A.S. | 18 | 4 | 2 | 53 | 0.39 | 39 | 23 | 1 | 2.5 |
| 5 | K.H. | 78 | 64 | 1 | 6 | 0.66 | 63 | 62 | 25 | 17 |
| 6 | M.R.B. | 61 | 43 | 1 | 19 | 5.00 | 27 | 18 | 4 | 5 |
| 7 | L.M. | 61 | 45 | 2 | 19 | 0.73 | 36 | 22 | 1 | 2.7 |
| 8 | S.B.D. | 48 | 43 | 2 | 6 | 1.90 | 20 | 24 | 20 | 4 |
| 9 | W.P. | 49 | 37 | 8 | 11 | 1.00 | 76 | 52 | 9 | 3.4 |
| 10 | W.S. | 64 | 61 | 1 | 4 | 2.80 | 16 | 30 | 5 | 8 |

*These cases are a random series of cases, without knowledge of age, stage of disease, or treatment.
Proportions of total lymphoid cells and $CD19^+$ cells are expressed as percentages of all events in the listmode file. NK ($CD56^+$) and T($CD3^+$) cells are expressed as percentages of lymphocytes. The subsets of $CD11b^+/CD8^+$ T cells are shown as the percentage of all CD8+ T cell. "%" normal values, if known, are in parentheses.

If a therapeutic intervention is restricted to only those cells that co-express CD11b and CD3, it is important to establish what percentage of granulocytes, NK cells, and T-helper cells co-express these two markers.

In 4 of 6 cases of Chronic Lymphocytic Leukemia (CLL), less than 1% of granulocytes co-express CD11b and CD3, while in the other 2 cases 9.5% and 7% of granulocytes co-express these molecules (see, Table 1).

This data shows that a very small percentage of $CD3^+/CD11b^+$ cells are T-helper (i.e., $CD4^+$) cells. Thus, $CD8^+/CD11b^+$ are equivalent to $CD8^+/CD3^+$ populations.

Although the invention has been described with reference to the above examples, it will be understood that modifications and variations are encompassed within the spirit and scope of the invention. Accordingly, the invention is limited only by the following claims.

What is claimed is:

1. A method for the treatment of B-cell chronic lymphocytic leukemia (B-CLL) in a subject, comprising administering to the subject, in an amount effective for the treatment, a pharmaceutical composition comprising (a) at least one multivalent polypeptide that (i) immunospecifically binds CD3 and CD11b surface markers simultaneously expressed on the surface of a regulatory T cell and (ii) exerts a cytostatic or cytotoxic effect on a subpopulation of regulatory T cells; and (b) a pharmaceutically acceptable carrier.

2. The method of claim 1, wherein the multivalent polypeptide comprises an antibody or fragments thereof.

3. The method of claim 2, wherein the antibody is humanized or chimeric.

4. The method of claim 2, wherein the antibody is a bispecific antibody.

5. The method of claim 1, wherein the multivalent polypeptide is conjugated to a cytotoxic agent.

6. The method of claim 5, wherein the cytotoxic agent is a radionuclide.

7. The method of claim 6, wherein the radionuclide is selected from the group consisting of $P^{32}$, $P^{33}$, $Sc^{47}$, $Cu^{64}$, $Cu^{67}$, $As^{77}$, $Y^{90}$, $PH1^{05}$, $Pd^{109}$, $Ag^{111}$, $I^{125}$, $Pr^{143}$, $Sm^{153}$, $Tb^{161}$, $Lu^{177}$, $Re^{186}$, $Re^{188}$, $Re^{189}$, $Ir^{194}$, $Au^{199}$, $Pb^{212}$, and $Bi^{213}$.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic construct: linker

<400> SEQUENCE: 1

Gly Gly Gly Gly Ser Gly Gly Gly Gly Ser Gly Gly Gly Gly Ser
1               5                   10                  15